United States Patent [19]

Leininger et al.

[11] Patent Number: 4,692,527

[45] Date of Patent: Sep. 8, 1987

[54] 2-AMINO-3,5-DI-(HALOMETHYL)-PYRAZINES AND THEIR PREPARATION

[75] Inventors: Hartmut Leininger, Neustadt; Wolfgang Littmann, Mannheim; Joachim Paust, Neuhofen; Walter Trautmann, Neustadt, all of Fed. Rep. of Germany

[73] Assignee: BASF Aktiengesellschaft, Ludwigshafen, Fed. Rep. of Germany

[21] Appl. No.: 776,460

[22] Filed: Sep. 16, 1985

[30] Foreign Application Priority Data

Sep. 15, 1984 [DE] Fed. Rep. of Germany ....... 3433959

[51] Int. Cl.$^4$ .................. C07D 403/04; C07D 241/20
[52] U.S. Cl. .................................... 544/405; 544/336
[58] Field of Search ................................ 544/336, 405

[56] References Cited

U.S. PATENT DOCUMENTS 3,320,126  5/1967  Meltzer .............................. 514/255

FOREIGN PATENT DOCUMENTS 1493752 11/1965  Fed. Rep. of Germany .
3242195 11/1982  Fed. Rep. of Germany .

OTHER PUBLICATIONS

Hirschberg, et al., J. Organic Chem., vol. 26, (1961) pp. 2356–2360.
Sharp, et al., Chem. Abstracts, vol. 46, (1952), entry 2083h.
E. C. Taylor et al., J. Org. Chem. vol. 43, No. 4, 1978, p. 736.
E. C. Taylor et al., J. Org. Chem. 45, 1980, pp. 2485 to 2489.
E. C. Taylor et al., J. Org. Chem. 46, 1981, pp. 1394 to 1402.
Houben-Weyl, Methoden der Org. Chemie, vol. 5/3, Georg-Thieme Verlag Stuttgart, 1962, pp. 728, 731, 748.

Primary Examiner—Donald G. Daus
Assistant Examiner—William A. Teoli, Jr.
Attorney, Agent, or Firm—Oblon, Fisher, Spivak, McClelland & Maier

[57] ABSTRACT

2-Amino-3,5-di-(halomethyl)-pyrazines of the general formula I

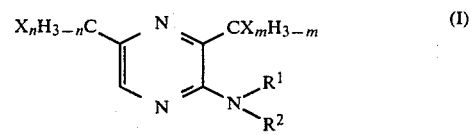

where X is either chlorine or bromine, m and n may each be 0, 1, 2 or 3 and $R^1$ and $R^2$ are each hydrogen or a protective group or may furthermore be bonded to one another, in particular those compounds of the formula I in which m is 1 and n is 2 and/or $R^1$ and $R^2$ together form a phthaloyl radical, are useful intermediates for the pteridine building block of folic acid or folic acid analogs.

They are obtained by a method in which a 2-amino-3,5-dimethylpyrazine of the general formula II

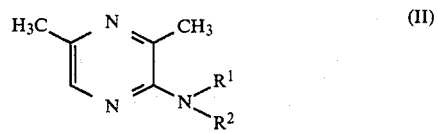

is treated with a chlorinating or brominating agent and, where $R^1$ and/or $R^2$ are protective groups, these are, if desired, eliminated when the chlorination or bromination is complete.

3 Claims, No Drawings

2-AMINO-3,5-DI-(HALOMETHYL)-PYRAZINES AND THEIR PREPARATION

The present invention relates to 2-amino-3,5-di-(halomethyl)-pyrazines of the general formula I

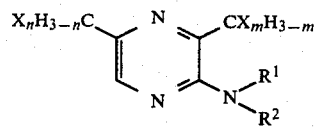

where X is chlorine or bromine, m and n may each be 0, 1, 2 or 3, and $R^1$ and $R^2$ are each hydrogen or a protective group and may furthermore be bonded to one another, preferably those pyrazines of the formula I where m is 1 and n is 2, in particular those in which m is 1, n is 2 and $R^1$ and $R^2$ together form a phthaloyl radical.

The present invention furthermore relates to a process for the preparation of the compounds I.

It was a general object of the invention to make the physiologically important compound folic acid

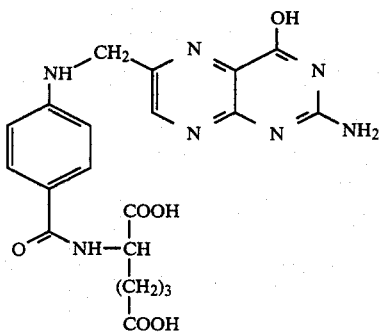

and its derivatives more readily available. In particular, the object related to new intermediates having the 2-aminopyrazine structure which on the one hand are readily obtainable and on the other hand can be converted in a relatively simple manner to reactive pteridines and further to folic acid or its derivatives.

E. C. Taylor et al (J. Org. Chem., Vol. 43 (1978), No. 4, 736) disclosed that 6-formylpterin of the formula

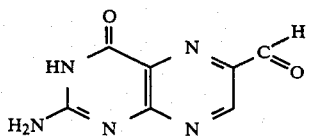

which is a key compound for folic acid and a very large variety of derivatives of this, can be prepared in a relatively simple manner and in good yields from 2-amino-3-cyano-5-dialkoxymethylpyrazine. However, the starting compound envisaged in this publication for the preparation of the 2-amino-3-cyano-5-dialkoxymethylpyrazine, ie. 2-amino-3-cyano-5-chloromethylpyrazine, is unfortunately itself not readily obtainable. It is obtained, for example, in only moderate yields from aminomalononitrile and β-chloropyruvaldoxime, which in turn can be prepared from ketene and is a physiologically extremely unpleasant substance which decomposes at room temperature with formation of hydrocyanic acid and is therefore unsuitable for an industrial reaction (cf. E. C. Taylor et al., J. Org. Chem. 38 (1973), 806). In spite of great efforts by E. C. Taylor et al. (cf. J. Org. Chem. 45 (1980), 2485–2489, and J. Org. Chem. 46 (1981), 1394–1402), it has not been possible to provide an industrially usable process for the preparation of pure isomer-free 2-amino-3-cyano-5-dialkoxymethylpyrazines, so that to date the latter were known only as substances which were difficult to obtain and could be prepared only in poor yields, in a large number of stages and/or from starting materials which were expensive or not readily synthesizable.

It is an object of the present invention to provide novel intermediates having the 2-amino-pyrazine structure which on the one hand are readily obtainable and on the other hand can be converted in a relatively simple manner to 2-amino-3-cyano-5-dialkoxymethylpyrazine, permitting an advantageous overall process for the preparation of folic acid and its derivatives via 6-formylpterin.

We have found that this object is achieved and that, surprisingly, 2-amino-3,5-di-(halomethyl)-pyrazines of the general formula I are obtained in good yields if the corresponding 2-amino-3,5-dimethylpyrazines of the general formula II

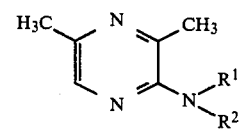

are treated with a chlorinating or brominating agent and, where $R^1$ and/or $R^2$ are protective groups, these are, if desired, eliminated when the chlorination or bromination is complete.

The parent compound of the starting compounds II (where $R^1$ and $R^2$ are each H) is known, and is obtainable in a relatively simple manner by the process described in German Laid-Open Application DOS No. 3,242,195, by cyclization of α-iminodipropionitrile of the formula III

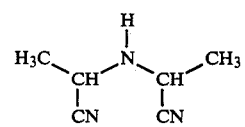

with a hydrogen halide. III in turn can be prepared by the reaction of ammonia with acetaldehyde and hydrocyanic acid, as described in German Laid-Open Application DOS No. 1,493,752.

On the other hand, the novel 2-amino-3,5-di-(halomethyl)-pyrazines of the formula I can be converted to useful intermediates of folic acid or of folic acid derivatives in a relatively simple and advantageous manner, for example by the method described in a patent application submitted simultaneously (O.Z. No. 0050/37334; P No. 34 33 960.4).

That the novel halogenation of the 2-amino-3,5-dimethylpyrazines II to the compounds of the formula I, in particular those of the formula I where m is 1 and n is 2, was successful at all, and furthermore gave such good yields, was not to be expected and was very surprising. The statements in standard works of chemistry about the problem of halogenation of nitrogen-containing heterocycles show this in a convincing manner. For example, Houben-Weyl, Methoden der organischen Chemie, volume 5/3, Georg-Thieme Verlag Stuttgart, 1962, page 728 states in connection with chlorination of the nucleus: "The chlorination of pyridines and pyridine derivatives generally results in low yields of more highly chlorinated products, which contain increasing amounts of tar-like constituents as the temperature increases". This would mean, a priori that secondary reactions, such as chlorination of the nucleus, as well as uncontrolled further reactions were to be expected. Furthermore, it is stated on page 731 that "pyrazine cannot be chlorinated at room temperature but only at elevated temperatures"; in connection with the process of the patent application, the question arose as to what influence the various substituents may have on the halogenation.

Furthermore, page 748 may be cited regarding the statements on the halogenation of side chains of aromatics; on this page, it is stated that "β-picoline, 3-methylquinoline, lepidine, and 1-, 3- and 4-methylisoquinoline cannot be chlorinated directly in the side chain" and, regarding the chlorination of picoline, "since the chlorination proceeds directly to the trichloro stage . . . " and "α-picoline and γ-picoline can be chlorinated in the side chain, but not brominated". From all of these statements, the average skilled worker would have to assume that both the halogenation as such, the chlorination and in particular the bromination, would not take place at all successfully or would merely lead to perchlorinated products. Furthermore, where the compounds of the formula II were used as starting compounds, complications in connection with the nonequivalence of the two methyl groups would have to be feared, since ibid. page 748 discloses that "chlorination of 3,4,5-trimethylpyrazole in glacial acetic acid gives 4-methyl-3,5-bistrichloromethylpyrazole in a yield of 74%. In 1,3,5-trimethylpyrazole on the other hand . . . only one methyl group is substituted."

In summary, it may be stated that, on the basis of the prior art, it was not to be expected that it will be possible to convert the 2-amino-3,5-dimethylpyrazines II by chlorination or bromination to the 2-amino-3,5-di-(halomethyl)-pyrazines of the formula I in such good yields, hence permitting the industrial preparation of pure, isomer-free intermediates for pteridine syntheses, as are otherwise extremely difficult to synthesize and to date cannot be synthesized on an industrial scale.

For the chlorination or bromination (referred to below as halogenation), it is advisable in general to protect the amino group of the 2-amino-3,5-dimethylpyrazine in a conventional manner. Suitable protective groups are the conventional groups also known from peptide chemistry, such as the carbobenzyloxy, carbo-tert.-butoxy, triphenylmethyl, p-toluenesulfonyl, formyl, trifluoroacetyl, carbo-p-nitrobenzyloxy and phthaloyl groups.

o-Phthalic acid is particularly suitable for protecting the 2-amino group, the phthalimide group, which is very chemically stable to oxidation, being formed.

To introduce this protective group, the free 2-amino compound II is reacted with phthalic anhydride, advantageously at from 80° to 120° C. in the presence of an inert solvent, and the water eliminated in the process is removed continuously from the reaction mixture together with the solvent by azeotropic distillation. Examples of suitable solvents for this purpose are benzene, toluene, the xylenes and chlorobenzene.

The amino group can also be monoacylated or diacylated in a similar manner with other carboxylic or sulfonic acids, preferably with strong ones, for example with the tert.-butyl ester, the benzyl ester or the p-nitrobenzyl ester of chlorocarbonic acid, formic acid, trifluoroacetic acid or p-toluenesulfonic acid.

Other protective groups, such as the triphenylmethyl group, which is obtained by reacting triphenylmethyl chloride with the free amino compound II, are also suitable. The free amino compound III may also be subjected to the process, but in this case losses in the yield of I as a result of side reactions must be expected.

The halogenation takes place in accordance with the known laws of side-chain halogenation of aromatic compounds, preferably in the presence of an inert solvent, such as carbon tetrachloride or chlorobenzene, at from 20° to 132° C., preferably at the boiling point of the mixture with refluxing of the solvent.

Particularly suitable halogenating agents are chlorine and bromine, as well as, for example, N-chloro-and N-bromosuccinimide, dichlorine monoxide, sulfuryl chloride and thionyl chloride.

Since side chain halogenation is known to take place mainly via a free radical mechanism, the presence of catalytic amounts of free radical formers, such as benzoyl peroxide or azodiisobutyronitrile, is advisable in order to accelerate and complete the reaction. Instead of the free radical formers, or in addition to these, it is also possible to allow UV light to act on the reaction mixture.

In the extreme case, the halogenation product obtained may be a mixture of as many as 16 different chlorine or bromine compounds I. Examples of compounds of the formula I where $R^1$ and $R^2$ are each H or $R^1$ and $R^2$ together form the phthaloyl group are: 5-chloromethyl-3-methyl-2-phthalimidopyrazine, 3-chloromethyl-5-methyl-2-phthalimidopyrazine, 3,5-bis-(chloromethyl)-2-phthalimidopyrazine, 5-dichloromethyl-3-methyl-2-phthalimidopyrazine, 3-dichloromethyl-5-methyl-2-phthalimidopyrazine, 5-chloromethyl-3-dichloromethyl-2-phthalimidopyrazine, 3-chloromethyl-5-dichloromethyl-2-phthalimidopyrazine, 3,5-bis-(dichloromethyl)-2-phthalimidopyrazine, 3-methyl-2-phthalimido-5-trichloromethylpyrazine, 3-chloromethyl-2-phthalimido-5-trichloromethylpyrazine, 3-dichloromethyl-2-phthalimido-5-trichloromethylpyrazine, 3-bromomethyl-5-methyl-2-phthalimidopyrazine, 5-bromomethyl-3-methyl-2-phthalimidopyrazine, 3,5-bis(bromomethyl)-2-phthalimidopyrazine, 5-dibromomethyl-3-methyl-2-phthalimidopyrazine, 3-bromomethyl-5-dibromomethyl-2-phthalimidopyrazine and 3,5-bis-(dibromomethyl)-2-phthalimidopyrazine or the corresponding unprotected 2-amino analogs.

In the halogenation, it is also possible, if desired, preferentially to synthesize individual products. This is done, for example, by carrying out the novel process using the optimum stoichiometry for the desired product, or by carrying out the reaction using an excess of halogenating agent and terminating the reaction at the optimum time.

It is noteworthy that particularly important compounds of the formula I are those for which the relationship $n = m + 1$ holds, ie. the principal products, depending on reaction conditions, amount of halogenating agent and reaction time, are the 3-methyl-5-monochloromethyl, the 3-monochloromethyl-5-dichloromethyl and the 3-dichloromethyl-5-trichloromethyl compounds I or the corresponding bromine compounds.

Regarding the further reaction of I, the 3-monochloromethyl-5-dichloromethyl compounds or the corresponding bromine compounds Ia (where m is 2 and n is 1) are the most important, so that, on the basis of the above laws, it is possible to interrupt the halogenation, for example by cooling, precisely at this stage, before the average degree of halogenation of the two methyl groups increases further.

It is only important that the reaction be terminated at the stage where Ia is present in relatively the largest amount. This amount can readily be determined in preliminary experiments, for example by NMR spectroscopy or HPLC analysis. Once the optimum reaction time has been determined in this manner, no such analytical monitoring is required when the process is carried out on an industrial scale. In this way, yields of 69%, based on II, of the particularly important compounds of the formula 1 can be obtained.

Because Ia and the other equally preferentially obtainable compounds which are characterized by the relationship n=m+1 are present in large amounts, working up the reaction mixture to obtain these products presents no difficulties since they crystallize preferentially from virtually all solvents. The remaining compounds can, if desired, then be obtained in a conventional, although less simple, manner by crystallization from the mother liquors.

Suitable solvents for the crystallization include $C_1$-$C_4$-alkanols, eg. isopropanol, ketones, such as acetone, halohydrocarbons, such as methylene chloride, aromatic hydrocarbons, such as toluene, and acetonitrile. After crystallization has been carried out only once, the principal product, as a rule Ia, is obtained in a purity greater than 80%, which is usually sufficient for most further reactions. Higher purities can be achieved in a conventional manner by further recrystallization processes.

Frequently, however, a purity of from 60 to 80% is sufficient, since the subsequent products of Ia are as a rule easier to separate off from the remaining components of the reaction mixture than is Ia itself from the other compounds I.

For special or analytical purposes, all halogenation products I can be obtained in highly pure form by column chromatography. This is preferably carried out using silica gel having a particle diameter of from 0.02 to 0.2 mm as the solid phase, and a mixture of 5 parts by volume of 1,2-dichloroethane and 1 part by volume of ethyl acetate as the mobile phase.

The protective groups of I can be eliminated in a conventional manner, for example by reaction with hydrazine, before or after the purification by crystallization or chromatography.

However, since the compounds I are usually employed for further syntheses in which it is also advisable to protect the 2-amino group, the protective groups are as a rule not eliminated.

From the compounds Ia, by conventional substitution of the halogen radical, it is possible to obtain the corresponding compounds containing a —CH₂OH, —CHO or —COOH group and the ethers, acetals, nitriles and esters derived from these. For example, the pteridine building block of folic acid is obtained from Ia by the following route:

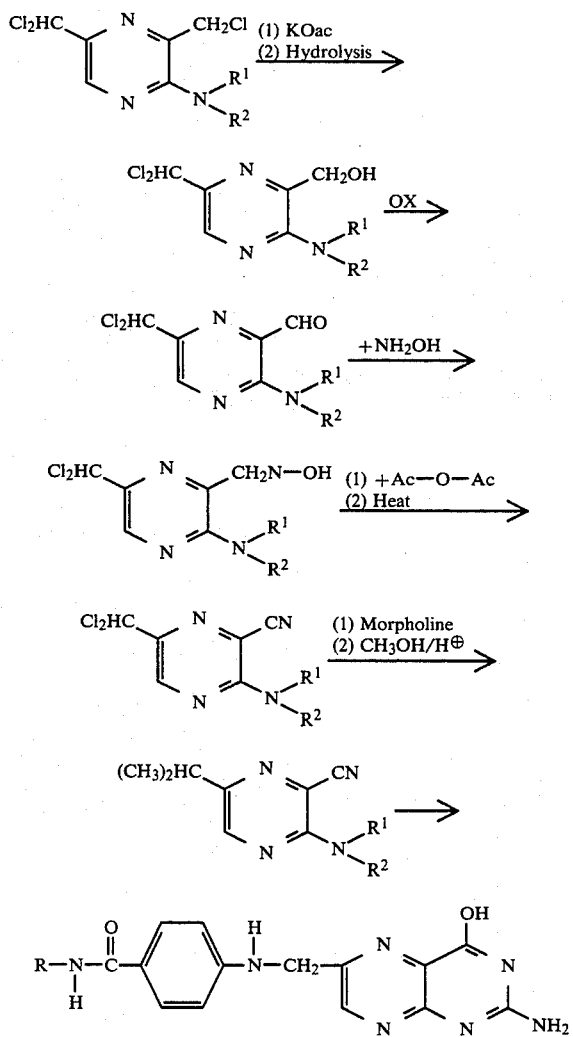

EXAMPLE 1

(a) Preparation of 3,5-dimethyl-2-phthalimidopyrazine 481 g of phthalic anhydride were added to a solution of 307 g of 2-amino-3,5-dimethylpyrazine and 1100 g of chlorobenzene at 25° C., and the mixture was heated at the boil for 6 hours, the water of reaction being removed continuously.

When the reaction was complete, 1 l of water was added to the resulting brown solution, after which the chlorobenzene was distilled off together with water, while keeping the volume of water constant. A further 0.5 l of water was then added to the remaining aqueous solution, and the mixture was heated to the boil and then cooled to 25°-30° C., the product being precipitated. The mixture obtained was stirred for a further 2 hours at this temperature, after which the product was isolated and taken up in 1.5 l of boiling methanol, the solution was cooled to 0° C. and the product was then filtered off. The yield was virtually quantitative, and the melting point was 142°-143° C.

(b) Chlorination of 3,5-dimethyl-2-phthalimidopyrazine 7.5 ml of a solution of 0.42 g of azodiisobutyronitrile in chlorobenzene were added to a solution of 63.2 g (0.25 mole) of the pyrazine obtained as described in (a), in 250 ml of chlorobenzene, at 95° C., and 107 g (3 equivalents) of chlorine were passed into the reaction mixture in the course of 4 hours at 100° C. After from 2.5 to 3.5 hours, a further 0.42 g of azodiisobutyronitrile was added.

The chlorobenzene was then distilled off at 80° C., and the residue was recrystallized from 260 ml of isopropanol. The yield of the chlorination products was 69 g.

NMR spectroscopy and HPLC analysis showed that the mixture consisted of

42% of 3-chloromethyl-5-dichloromethyl-2-phthalimidopyrazine (m=1 and n=2),
29% of 3,5-bis-(dichloromethyl)-2-phthalimidopyrazine (m=2 and n=2),
21% of 3-dichloromethyl-5-chloromethyl-2-phthalimidopyrazine and a total of
8% of the compounds 3-dichloromethyl-5-trichloromethyl-2-phthalimidopyrazine, 3-methyl-5-dichloromethyl-2-phthalimidopyrazine, 3,5-bis-(chloromethyl)-2-phthalimidopyrazine and 3-methyl-5-chloromethyl-2-phthalimidopyrazine.

The crude crystalline product was taken up in 130 ml of hot acetone. When the solution was cooled, 33.0 g of a product mixture containing 62% of 3-chloromethyl-5-dichloromethyl-2-phthalimidopyrazine were obtained. Recrystallization from dichloromethane increased the amount of 3-chloromethyl-5-dichloromethyl-2-phthalimidopyrazine to 80% and gave a yield of 14.3 g.

Toluene was added to the mother liquor from the acetone treatment, and the mixture was freed from acetone and cooled to room temperature. 18.3 g of a product mixture containing 60% of 3,5-bis(dichloromethyl)-2-phthalimidopyrazine were obtained.

EXAMPLE 2

Reaction of 3,5-dimethyl-2-phthalimidopyrazine with N-chlorosuccinimide 1.00 g of benzoyl peroxide (containing 25% of water) was dissolved in 100 ml of chloroform, and the organic phase was separated off and dried with sodium sulfate. 5.06 g (0.02 mole) of 3,5-dimethyl-2-phthalimidopyrazine and 21.4 g (0.16 mole) of N-chlorosuccinimide were added to the solution, the reaction mixture was refluxed for 72 hours and then cooled to room temperature, and the precipitated crystals were filtered off under suction. When the mother liquor had been evaporated down, the resulting crystalline mass was purified by means of chromatography over silica gel.

The first fraction (1.22 g) contained a product mixture consisting of 71% of 3-methyl-5-chloromethyl-2-phthalimidopyrazine, 25% of 3-chloromethyl-5-methyl-2-phthalimidopyrazine and 4% of 3,5-bis(chloromethyl)-2-phthalimidopyrazine. On the other hand, the second fraction (2.00 g) contained the products in the following ratio: 61.2% of 3-methyl-5-chloromethyl-2-phthalimidopyrazine, 37% of 3-chloromethyl-5-methyl-2-phthalimidopyrazine and 2% of 3,5-bis(chloromethyl)-2-phthalimidopyrazine.

EXAMPLE 3

Reaction of 3,5-dimethyl-2-phthalimidopyrazine with dichlorine monoxide

A solution of 41.4 g (0.48 mole) of dichlorine monoxide in 1350 ml of carbon tetrachloride was added dropwise to a solution of 58.9 g (0.23 mole) of 3,5-di-methyl-2-phthalimidopyrazine in 100 ml of carbon tetrachloride. The reaction mixture was heated to 40° C., after which it was stirred at room temperature for 14 hours and then evaporated down. The viscous oil which remained was taken up in 5:1 1,2-dichloroethane/ethyl acetate, and the solution was chromatographed over silica gel.

The first fraction (9.46 g) contained a 3:1 mixture of 3-methyl-5-chloromethyl-2-phthalimidopyrazine and 3-chloromethyl-5-methyl-2-phthalimidopyrazine, and the second fraction (4.89 g) contained a 1.6:1 mixture of 3-methyl-5-chloromethyl-2-phthalimidopyrazine and 3-chloromethyl-5-methyl-2-phthalimidopyrazine.

27.14 g (0.11 mole) of the 3,5-dimethyl-2-phthalimidopyrazine employed were recovered.

EXAMPLE 4

Bromination of 3,5-dimethyl-2-phthalimidopyrazine 83 g of potassium carbonate and 1.15 g of azodiisobutyronitrile were added to a solution of 50.6 g (0.2 mole) of 3,5-dimethyl-2-phthalimidopyrazine in 2000 ml of chlorobenzene. A solution of 64 g (0.8 equivalent) of bromine in 200 ml of chlorobenzene was added dropwise, in the course of 8.5 hours, to the resulting reaction mixture, with exposure to UV light and refluxing. The mixture was then refluxed for a further 12 hours, after which it was filtered, and evaporated down under reduced pressure (1 mbar). The product was recrystallized from acetonitrile, 57 g of a crystalline product having the following composition according to the $^1$H-NMR spectrum (270 MHz, CDCl$_3$) were obtained:

4% of 3-bromomethyl-5-methyl-2-phthalimidopyrazine,
18% of 5-bromomethyl-3-methyl-2-phthalimidopyrazine,
7% of 3,5-bis-(bromomethyl)-2-phthalimidopyrazine,
53% of 5-dibromomethyl-3-methyl-2-phthalimidopyrazine,
16% of 3-bromomethyl-5-dibromomethyl-2-phthalimidopyrazine and
2% of 3,5-bis-(dibromomethyl)-2-phthalimidopyrazine.

We claim:

1. A 2-amino-3,5-di-(halomethyl)-pyrazine of the formula I

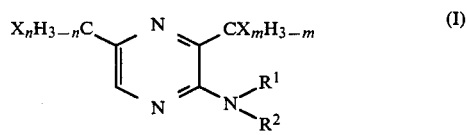

where X is either chlorine or bromine, m is 1 or 2 and n is =m+1, and R$^1$ and R$^2$ are each hydrogen or together form a phthalimido radical.

2. A 2-amino-3,5-di-(halomethyl)-pyrazine of the formula I as claimed in claim 1, in which m is 1, n is 2 and R$^1$ and R$^2$ together form a phthalimido radical.

3. A A 2-amino-3,5-di-(halomethyl)-pyrazine of the formula I as claimed in claim 1, which is selected from the group consisting of 3-monochloromethyl-5-dichloromethyl, 3-dichloromethyl-5-trichloromethyl, 3-monobromomethyl-5-dibromomethyl, and 3-dibromomethyl-5-tribromomethyl compounds I.

* * * * *